US010539520B2

(12) United States Patent
Murakami

(10) Patent No.: US 10,539,520 B2
(45) Date of Patent: Jan. 21, 2020

(54) SAMPLE-ANALYZING SYSTEM

(71) Applicant: SHIMADZU CORPORATION, Kyoto-shi, Kyoto (JP)

(72) Inventor: Sachio Murakami, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 121 days.

(21) Appl. No.: 15/484,529

(22) Filed: Apr. 11, 2017

(65) Prior Publication Data

US 2017/0307551 A1 Oct. 26, 2017

(30) Foreign Application Priority Data

Apr. 21, 2016 (JP) ................................ 2016-084964

(51) Int. Cl.
*G01N 23/223* (2006.01)
*G01N 21/65* (2006.01)
(Continued)

(52) U.S. Cl.
CPC ....... *G01N 23/223* (2013.01); *G01N 21/3103* (2013.01); *G01N 21/35* (2013.01);
(Continued)

(58) Field of Classification Search
CPC ...... G01N 23/223; G01N 21/73; G01N 21/94; G01N 21/35; G01N 21/65; G06F 19/703; G01V 8/10

See application file for complete search history.

(56) References Cited

U.S. PATENT DOCUMENTS 5,130,559 A 7/1992 Leifeld et al.
2006/0029182 A1 2/2006 Tani et al.
(Continued)

FOREIGN PATENT DOCUMENTS

JP H06-337252 A 12/1994
JP 08-334481 A 12/1996
(Continued)

OTHER PUBLICATIONS

Extended European Search Report dated Jun. 11, 2018 issued by the European Patent Office in counterpart application No. 17203167.6.
(Continued)

*Primary Examiner* — Regis J Betsch
*Assistant Examiner* — Jeremy A Delozier
(74) *Attorney, Agent, or Firm* — Sughrue Mion, PLLC

(57) ABSTRACT

Provided is a sample-analyzing system used for identifying a target sample from its measurement data obtained using a plurality of analyzing devices including at least one device selected from a fluorescent X-ray analyzer, atomic absorption photometer and inductively coupled plasma emission analyzer as well as at least one device selected from an infrared spectrophotometer and Raman spectrophotometer. The system includes: a storage section for holding measurement data obtained for each of the reference objects using the analyzing devices; a measurement data comparator for comparing, for each analyzing device, the measurement data of the target sample with those of the reference objects and for determining the degree of matching of the target sample with each reference object; an integrated degree-of-matching calculator for calculating an integrated degree of matching from the degrees of matching determined for the analyzing devices; and a comparison result output section for outputting information concerning a predetermined number (Continued)

of reference objects in descending order of the integrated degree of matching.

2 Claims, 5 Drawing Sheets

(51) Int. Cl.
| | | |
|---|---|---|
| *G01N 21/73* | (2006.01) | |
| *G01N 5/00* | (2006.01) | |
| *G01N 21/31* | (2006.01) | |
| *G01N 21/35* | (2014.01) | |
| *G01V 8/10* | (2006.01) | |
| *G01V 5/00* | (2006.01) | |
| *G01N 21/94* | (2006.01) | |
| G01N 21/3563 | (2014.01) | |
| G01N 21/68 | (2006.01) | |
| G01N 33/02 | (2006.01) | |
| G16C 20/20 | (2019.01) | |

(52) U.S. Cl.
CPC ............. *G01N 21/65* (2013.01); *G01N 21/73* (2013.01); *G01N 21/94* (2013.01); *G01V 5/00* (2013.01); *G01V 8/10* (2013.01); *G01N 21/3563* (2013.01); *G01N 21/68* (2013.01); *G01N 33/02* (2013.01); *G01N 2021/3595* (2013.01); *G01N 2201/12* (2013.01); *G01N 2223/076* (2013.01); *G01N 2223/304* (2013.01); *G01N 2223/618* (2013.01); *G01N 2223/652* (2013.01); *G16C 20/20* (2019.02)

(56) References Cited

U.S. PATENT DOCUMENTS

| | | | |
|---|---|---|---|
| 2006/0291619 A1 | 12/2006 | Statham | |
| 2012/0062873 A1 | 3/2012 | Stewart et al. | |
| 2012/0072122 A1* | 3/2012 | Schweitzer | G06F 17/30536 702/19 |
| 2013/0208850 A1* | 8/2013 | Schmitt | G01N 23/20 378/4 |
| 2014/0005980 A1* | 1/2014 | Green | G01N 24/08 702/181 |
| 2014/0088876 A1* | 3/2014 | Shiley | G01V 13/00 702/8 |
| 2016/0292197 A1 | 10/2016 | Morimoto et al. | |

FOREIGN PATENT DOCUMENTS

| | | |
|---|---|---|
| JP | 2000-258340 A | 9/2000 |
| JP | 2001-074650 A | 3/2001 |
| JP | 2006-119108 A | 5/2006 |
| JP | 2007003532 A | 1/2007 |
| JP | 2007278746 A | 10/2007 |
| JP | 2010-223908 A | 10/2010 |
| JP | 2010-249845 A | 11/2010 |
| JP | 2015-153296 A | 8/2015 |
| JP | 2016-121019 A | 7/2016 |
| JP | 2016-176817 A | 10/2016 |
| WO | 2011/103161 A2 | 8/2011 |
| WO | 2015/079535 A1 | 6/2015 |

OTHER PUBLICATIONS

Communication dated Jun. 26, 2018 issued by the State Intellectual Property Office of People's Republic of China in counterpart application No. 201710259756.1.
Communication dated Sep. 5, 2017 from the European Patent Office in counterpart application No. 17165987.3.
Notice of Reasons for Refusal, dated Sep. 17, 2019, issued in corresponding JP Application No. 2016-084964, 4 pages with translation.
Non-Final Office Action, dated Oct. 3, 2019, issued in related U.S. Appl. No. 15/823,922, 21 pages.
Notice of Reasons for Refusal, dated Nov. 12, 2019, issued in related Japanese Application No. 2016-229745, 6 pages in English and Japanese.

* cited by examiner

Fig. 6

| Order | EDX | | FTIR | |
|---|---|---|---|---|
| | Reference Object | Degree of Matching | Reference Object | Degree of Matching |
| 1 | Reference_object_7 | 0.998 | Reference_object_2 | 0.999 |
| 2 | Reference_object_5 | 0.996 | Reference_object_5 | 0.895 |
| 3 | Reference_object_1 | 0.986 | Reference_object_6 | 0.886 |
| 4 | Reference_object_6 | 0.977 | Reference_object_7 | 0.862 |
| 5 | Reference_object_3 | 0.975 | Reference_object_3 | 0.858 |
| 6 | Reference_object_2 | 0.965 | Reference_object_10 | 0.856 |
| 7 | Reference_object_4 | 0.954 | Reference_object_9 | 0.835 |
| 8 | Reference_object_8 | 0.938 | Reference_object_1 | 0.828 |
| 9 | Reference_object_9 | 0.919 | Reference_object_8 | 0.814 |
| 10 | Reference_object_10 | 0.881 | Reference_object_4 | 0.799 |

Fig. 7

| Order | Reference Object | Integrated Degree of Matching |
|---|---|---|
| 1 | Reference_object_2 | 0.982 |
| 2 | Reference_object_5 | 0.946 |
| 3 | Reference_object_6 | 0.932 |
| 4 | Reference_object_7 | 0.930 |
| 5 | Reference_object_3 | 0.917 |
| 6 | Reference_object_1 | 0.907 |
| 7 | Reference_object_9 | 0.877 |
| 8 | Reference_object_4 | 0.877 |
| 9 | Reference_object_8 | 0.876 |
| 10 | Reference_object_10 | 0.869 |

Fig. 8

| Display Items | Report Output Layout |
|---|---|
| Name of reference object | Name of / Comment / Order / Degree of |
| Degree of matching | Camera image / EDX image |
| Order | EDX measurement conditions |
| Comment | |
| Camera image | EDX profile |
| EDX image | |
| EDX measurement conditions | EDX quantitative analysis result |
| EDX quantitative analysis result | FTIR measurement conditions |
| EDX profile | |
| FTIR measurement conditions | FTIR profile |
| FTIR profile | |

61 — Display Items column; 62 — Report Output Layout column

Fig. 9

Library List

| Reference Object ID | Reference Object Name | EDX | | | FTIR | | Other | |
| | | EDX Photo | EDX Data | Comment | FTIR Data | Comment | Camera Image | Comment |
|---|---|---|---|---|---|---|---|---|
| 1 | AAAA_1 | ✓ | ✓ | ✓ | ✓ | ✓ | ✓ | ✓ |
| 2 | AAAA_2 | ✓ | ✓ | ✓ | ✓ | ✓ | ✓ | ✓ |
| 3 | AAAA_3 | ✓ | ✓ | ✓ | unregistered | unregistered | ✓ | ✓ |
| 4 | AAAA_4 | ✓ | ✓ | ✓ | ✓ | ✓ | ✓ | ✓ |
| 5 | AAAA_5 | ✓ | ✓ | ✓ | ✓ | ✓ | ✓ | ✓ |
| 6 | BBBB_1 | unregistered | unregistered | unregistered | ✓ | ✓ | ✓ | ✓ |
| ... | ... | ... | ... | ... | ... | ... | ... | ... |

New Registration — 72

○ Name  ○ ID  ○ Free word    Search — 73

SAMPLE-ANALYZING SYSTEM

TECHNICAL FIELD

The present invention relates to a sample-analyzing system for identifying a target sample by comparing measurement data of the target sample with those of reference objects, where the measurement data of the target sample are obtained using a plurality of kinds of analyzing devices including at least one device selected from a fluorescent X-ray analyzer, atomic absorption photometer and inductively coupled plasma emission analyzer which are all suitable for an analysis of inorganic substances, as well as at least one device selected from an infrared spectrophotometer and Raman spectrophotometer which are both suitable for an analysis of organic substances.

BACKGROUND ART

If a food or similar product in which a piece of vinyl, metal or similar foreign object is mixed is shipped to the market, the trustworthiness of the product will be noticeably lowered. Accordingly, in factories or similar facilities, a contamination inspection of the product is performed. If a foreign object is found in the inspection of the product, the foreign object is analyzed to determine the kinds, amounts and other properties of the contained substances or elements. The foreign object is subsequently identified by using a reference object database to reveal its origin and mixture route.

An analyzing device that is suitable for an analysis of a piece of vinyl or similar foreign object made of an organic substance is the Fourier transform infrared spectrometer (FTIR). In the FTIR, the foreign object is irradiated with interference waves generated by a Michelson interferometer including fixed and movable mirrors, and the transmitted or reflected light is measured as an interferogram. By Fourier-transforming this interferogram, an absorption spectrum is obtained, with the horizontal axis representing the wavenumber and the vertical axis representing the intensity (e.g. absorbance or transmittance). On the absorption spectrum, infrared absorptions appear at the wavelengths corresponding to the amounts of vibration energy or rotation energy of various substances contained in the foreign object. Accordingly, by comparing the absorption spectral pattern of the foreign object with those of the various reference objects previously stored in the reference object database, the foreign object can be identified from the similarity of the contained substances (for example, see Patent Literature 1).

On the other hand, an analyzing device that is suitable for an analysis of a piece of metal or similar foreign object which contains an inorganic substance is the energy dispersive fluorescent X-ray analyzer (EDX). In the EDX, the foreign object is irradiated with X-rays to obtain a fluorescence spectrum. On this fluorescence spectrum, an X-ray fluorescence peak appears at a specific energy position to each element. Accordingly, it is possible to identify an element contained in the foreign object by determining the peak position on the fluorescence spectrum. The quantity of the identified element can be determined by two methods: the FP method (fundamental parameter method) and the calibration curve method. In the FP method, the quantitative value of each element is determined by reproducing the measured intensity of the X-ray fluorescence using a theoretical formula with an assumed composition of the principal components (for example, see Patent Literature 2 or 3). As compared to the calibration curve method which requires preparing a calibration curve by measuring a plurality of standard samples having the same composition and known content, the FP method is advantageous in that such a task is unnecessary and the analysis can be easily performed. Quantitative values determined by the FP method are commonly called "semi-quantitative values" to distinguish them from exact quantitative values determined by the calibration curve method. By comparing the semi-quantitative values of the elements in the foreign object determined by the FP method with those of the elements contained in the various reference objects previously stored in the reference object database, the foreign object can be identified from the similarity of the contained substances.

CITATION LIST

Patent Literature

Patent Literature 1: JP 2001-74650 A
Patent Literature 2: JP 8-334481 A
Patent Literature 3: JP 2010-223908 A

SUMMARY OF INVENTION

Technical Problem

As for a foreign object which contains both inorganic and organic substances, a conventional identifying method is to compare an absorption spectrum obtained using an FTIR with absorption spectra stored in a reference object database and to also compare a semi-quantitative determination result obtained using an EDX with semi-quantitative values stored in a reference object database. The identification of the foreign object using the FTIR is primarily based on the degree of matching of the organic substances, while the identification of the foreign object using the EDX is primarily based on the degree of matching of the inorganic substances. Therefore, in some cases, the result of the identification by FTIR differs from that of the identification by EDX. In such a case, the analysis operator needs to make a final judgment taking into account the identification results obtained using the two devices. Since this judgment relies on the experience of the analysis operator, an insufficiently skilled operator may incorrectly identify the same foreign object as different objects (for example, an analysis operator with a sufficient amount of knowledge on inorganic substances may incorrectly judge the result of an FTIR identification if the operator has an insufficient amount of knowledge on organic substances).

The previously described combination of the FTIR and EDX is one specific example of the analyzing devices. In some cases, an atomic absorption photometer or inductively coupled plasma emission analyzer is used as the suitable device for the analysis of inorganic substances. Additionally, a Raman spectrophotometer may be used as the suitable device for the analysis of organic substances. Three or more devices may also be simultaneously used to analyze a foreign object. Any of these variations is also accompanied by the aforementioned problem.

The problem to be solved by the present invention is to provide a sample-analyzing system capable of correctly identifying a target sample (e.g. foreign object) without relying on the skill of an analysis operator and regardless of whether the target sample is an organic or inorganic substance.

Solution to Problem

The present invention developed for solving the previously described problem is a sample-analyzing system used for identifying a target sample from measurement data of the target sample obtained using a plurality of analyzing devices including at least one device selected from a fluorescent X-ray analyzer, atomic absorption photometer and inductively coupled plasma emission analyzer as well as at least one device selected from an infrared spectrophotometer and Raman spectrophotometer, the system including:

a) a storage section in which measurement data obtained for each of a plurality of reference objects using each of the analyzing devices are stored;

b) a measurement data comparator for comparing, for each of the analyzing devices, the measurement data of the target sample with the measurement data of the plurality of reference objects and for determining the degree of matching of the target sample with each of the plurality of reference objects;

c) an integrated degree-of-matching calculator for calculating an integrated degree of matching for each of the plurality of reference objects by integrating the degrees of matching determined for the plurality of analyzing devices; and d) a comparison result output section for outputting information concerning a predetermined number of reference objects in descending order of the integrated degree of matching.

The integrated degree of matching can be determined, for example, by adding or averaging the degrees of matching determined for the respective analyzing devices. As will be described later, the nature of the target sample determined from the measurement data may also be reflected in the calculation of the integrated degree of matching.

Examples of the information concerning the reference objects outputted by the comparison result output section include the name and measurement data of the reference objects. The output can be produced in any appropriate form, such as a display on the screen of a display unit or an output through a printer.

In the sample-analyzing system according to the present invention, the storage section holds previously stored measurement data obtained for a plurality of reference objects using each of the plurality of analyzing devices including at least one device selected from a fluorescent X-ray analyzer, atomic absorption photometer and inductively coupled plasma emission analyzer which are all suitable for an analysis of inorganic substances, as well as at least one device selected from an infrared spectrophotometer and Raman spectrophotometer which are both suitable for an analysis of organic substances. For each analyzing device, the system compares the measurement data of the target sample with those of each reference object, and determines the degree of matching for each reference object. Additionally, the system calculates the integrated degree of matching for each reference object by integrating the degrees of matching determined for the respective analyzing devices, and outputs a piece of information concerning a predetermined number of reference objects in descending order of the integrated degree of matching. With this sample-analyzing system, a piece of information concerning a predetermined number of reference objects can be obtained in descending order of the integrated degree of matching without requiring an analysis operator to make any judgment. Therefore, the sample can be correctly identified without relying on the skill of the analysis operator and regardless of whether the target sample is an organic or inorganic substance.

In the sample-analyzing system according to the present invention, if a fluorescent X-ray analyzer is included in the plurality of analyzing devices, the measurement data obtained using the fluorescent X-ray analyzer contain data related to the Compton scattered radiation and Rayleigh scattered radiation of the target sample. In a measurement using a fluorescent X-ray analyzer, the intensity of the Compton scattered radiation increases with an increase in the percentage of organic substances (i.e. substances composed of C, H, O, N and other light-weight elements) in the target sample, while the intensity of the Rayleigh scattered radiation increases with an increase in the percentage of inorganic substances.

Accordingly, the sample-analyzing system according to the present invention may be configured as follows:

the plurality of analyzing devices include a fluorescent X-ray analyzer;

the system further includes:

e) a scattered radiation intensity ratio calculator for calculating the intensity ratio between Compton scattered radiation and Rayleigh scattered radiation from the measurement data of the target sample obtained using the fluorescent X-ray analyzer; and f) a coefficient determiner for determining, based on the intensity ratio, a coefficient for weighting the degrees of matching related to the fluorescent X-ray analyzer and the infrared spectrophotometer or the Raman spectrophotometer, and the integrated degree-of-matching calculator calculates the integrated degree of matching after applying the coefficient to the degrees of matching related to the fluorescent X-ray analyzer and the infrared spectrophotometer or the Raman spectrophotometer.

This mode of the sample-analyzing system determines a suitable coefficient for the nature of the target sample (inorganic substance, organic substance or their mixture) from the measurement data of the target sample obtained using the fluorescent X-ray analyzer, and calculates the integrated degree of matching for each reference object after applying the coefficient to the degrees of matching related to the fluorescent X-ray analyzer and the infrared spectrophotometer or Raman spectrophotometer. For example, the system can be configured to calculate the ratio between the intensity of the Compton scattered radiation and that of the Rayleigh scattered radiation (intensity of the Compton scattered radiation/intensity of the Rayleigh scattered radiation) from the measurement data obtained using the fluorescent X-ray analyzer, and determines the integrated degree of matching using the coefficient as follows: if the ratio is less than 1.0, the system identifies the sample as an inorganic substance and uses a coefficient which gives a higher degree of priority to the degree of matching related to the fluorescent X-ray analyzer; if the ratio is equal to or greater than 1.0 and less than 2.0, the system identifies the sample as a mixture of inorganic and organic substances, and uses a coefficient which gives equal weights to both the degree of matching related to the fluorescent X-ray analyzer and the degree of matching related to the infrared spectrophotometer (or Raman spectrophotometer); and if the ratio is greater than 2.0, the system identifies the sample as an organic substance and uses a coefficient which gives a higher degree of priority to the degree of matching related to the infrared spectrophotometer (or Raman spectrophotometer). In this manner, the system can provide a more correct value of the integrated degree of matching which reflects the degree of matching related to a suitable analyzing device for the nature of the target sample.

Advantageous Effects of the Invention

With the sample-analyzing system according to the present invention, it is possible to correctly identify a target sample without relying on the skill of an analysis operator and regardless of whether the sample is an organic or inorganic substance.

BRIEF DESCRIPTION OF DRAWINGS

FIG. 6 illustrates the integration analysis in the sample-analyzing system of the present embodiment.

FIG. 7 illustrates the result of the integration analysis in the sample-analyzing system of the present embodiment.

FIG. 8 is one example of the window for editing the layout for an output of a report in the sample-analyzing system of the present embodiment.

FIG. 9 is one example of the library window displayed by the sample-analyzing system of the present embodiment.

DESCRIPTION OF EMBODIMENTS

One embodiment of the sample-analyzing system according to the present invention is hereinafter described with reference to the attached drawings.

Figure 1:
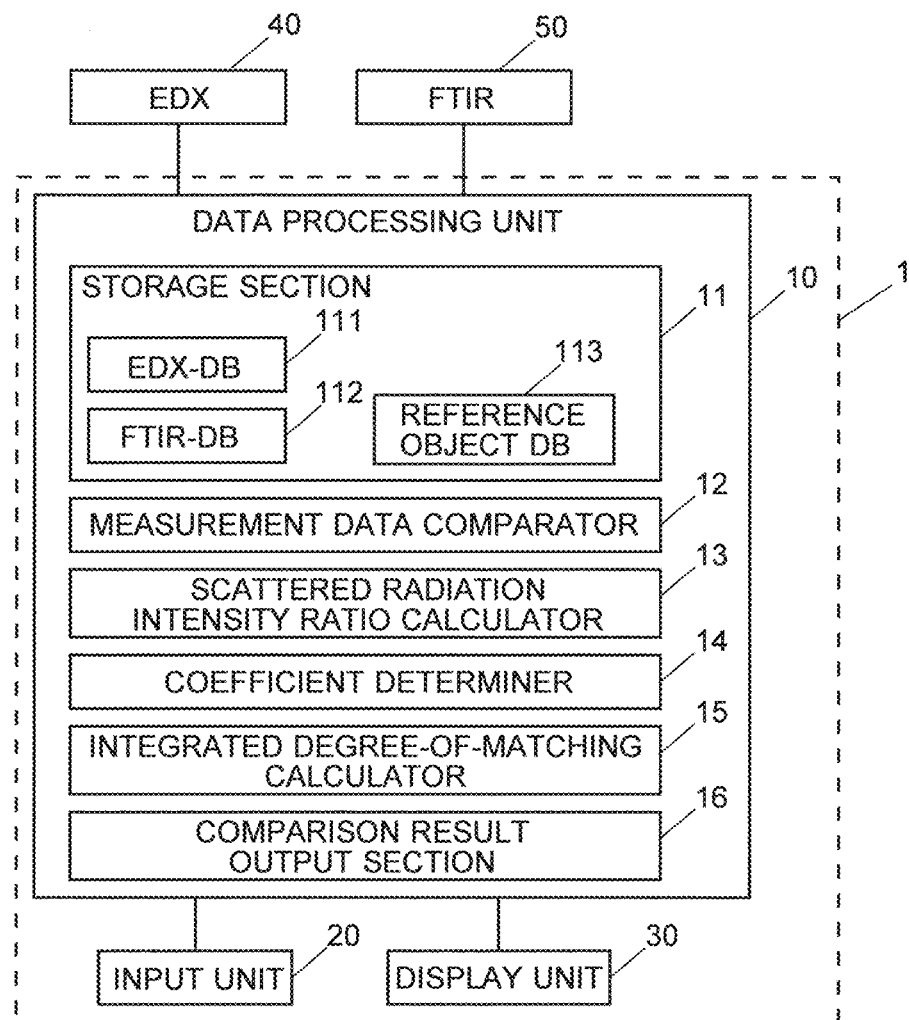
FIG. 1 is a configuration diagram showing the main components of a foreign-object analyzing system as one embodiment of the sample-analyzing system according to the present invention.

FIG. 1 shows the configuration of the main components of the sample-analyzing system of the present embodiment.

The sample-analyzing system 1 of the present embodiment includes a data processing unit 10, as well as an input unit 20 and display unit 30 connected to the data processing unit 10. The data processing unit 10 includes a storage section 11 and the following functional blocks: a measurement data comparator 12, scattered radiation intensity ratio calculator 13, coefficient determiner 14, integrated degree-of-matching calculator 15 and comparison result output section 16. The data processing unit 10 is actually a commonly used personal computer, with the aforementioned functional blocks embodied by running a sample-analyzing program on the CPU.

In the storage section 11, an energy dispersive fluorescent X-ray analysis database (EDX-DB) 111, Fourier transform infrared spectral database (FTIR-DB) 112 and reference object database (reference object DB) 113 are provided. Additionally, the data processing unit 10 is connected to a fluorescent X-ray analyzer (EDX) 40 and Fourier transform infrared spectrophotometer (FTIR) 50. Using these devices, the same unit 10 can perform a measurement on a sample and store the data obtained by the measurement in the data storage section 11.

Figure 2:
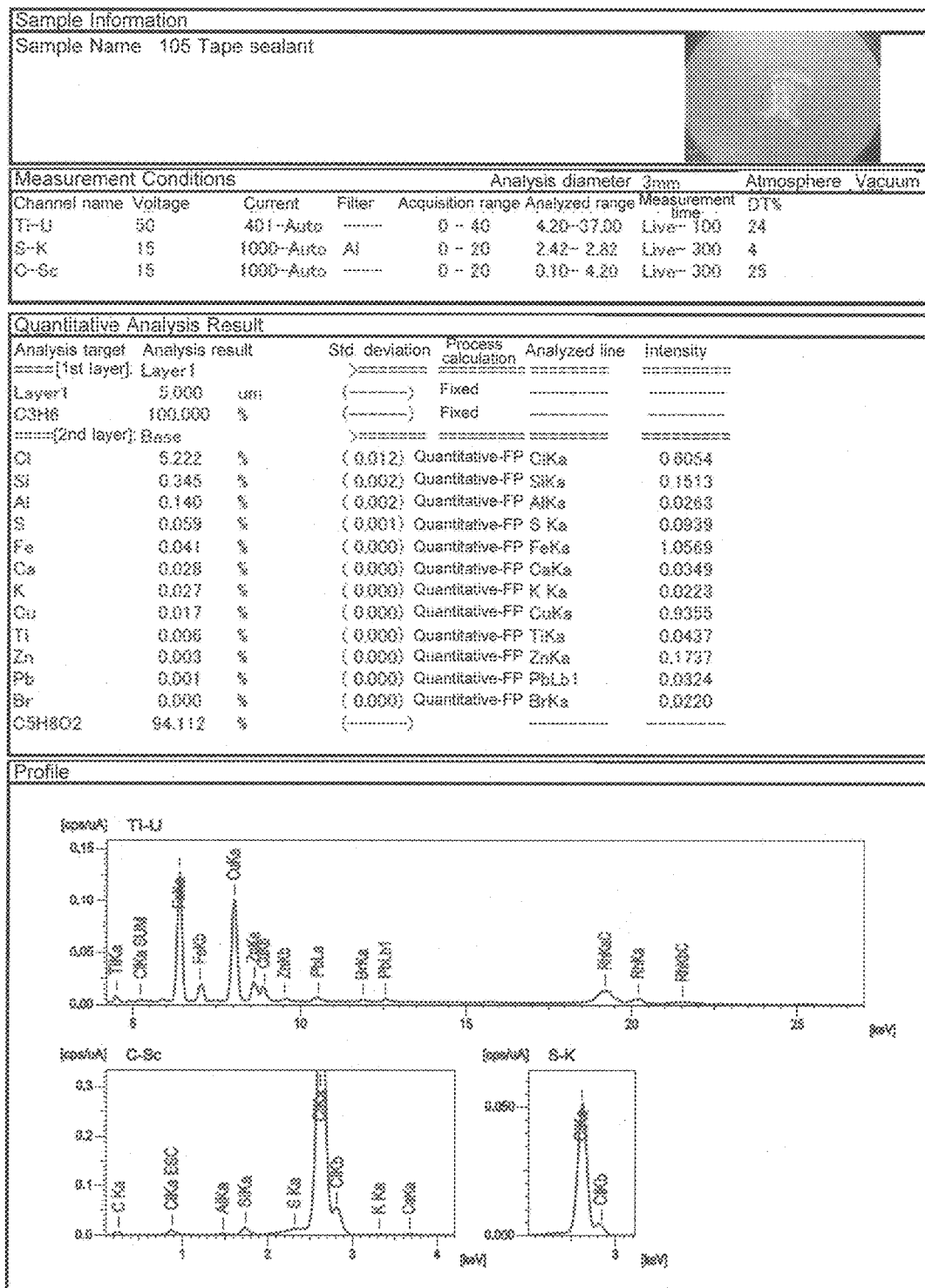
FIG. 2 is one example of the EDX data in the sample-analyzing system of the present embodiment.

The EDX-DB 111 contains measurement data obtained by a measurement performed on a plurality of reference objects using the EDX 40 (or another EDX). As shown in FIG. 2, the measurement data related to the EDX includes the ID number identifying the reference object, name of the reference object, image of the X-ray-irradiated portion taken with a camera provided in the EDX, measurement conditions, results of quantitative analyses, and profile (EDX spectrum data). A comment on the reference object (e.g. the measured portion of the reference object) put by the measurement operator is also included.

The FTIR-DB 112 contains measurement data obtained by a measurement performed on a plurality of reference objects using the FTIR 50 (or another FTIR). The measurement data related to the FTIR includes the ID number identifying the reference object, name of the reference object, measurement conditions, and spectrum data. A comment on the reference object put by the measurement operator is also included.

The reference object DB 113 contains data related to a plurality of reference objects themselves. Specifically, this DB contains the ID number identifying the reference object, name of the reference object, name and amount (or content ratio) of each element and/or compound contained in the reference object, photograph (camera image) of the reference object, as well as a comment on the reference object, e.g. when and where the reference object was obtained.

A procedure for identifying a foreign object (target sample) detected in a contamination inspection of the product, based on the measurement data obtained using the EDX 40 and FTIR 50, is hereinafter described with reference to FIGS. 3-7.

The user previously obtains measurement data (EDX data and/or FTIR data) of the foreign object and saves them in the storage section 11.

Figure 3:
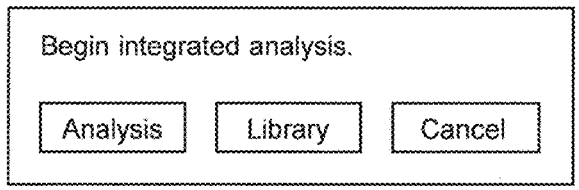
FIG. 3 is one example of the initial window displayed by the sample-analyzing system of the present embodiment.

Subsequently, the user commands the system to execute the sample-analyzing program, whereupon the system displays three options: "Analysis", "Library" and "Cancel", as shown in FIG. 3. If the user operating the input unit 20 selects "Analysis", the system initiates the analysis of the foreign object. If the user selects "Library", the system allows the user to view or edit the measurement data of the plurality of reference objects and other items of information stored in the EDX-DB 111, FTIR-DB 112 and reference object DB 113, as well as add measurement data of a new reference object (or other items of information) or delete some of the existing data. Selecting "Cancel" terminates the sample-analyzing program.

Figure 4:
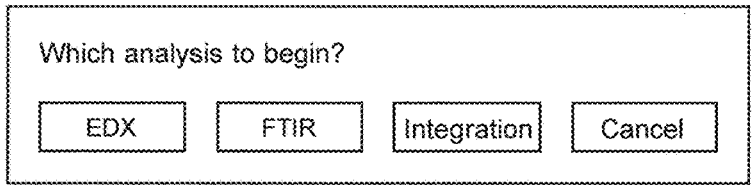
FIG. 4 is one example of the analysis window displayed by the sample-analyzing system of the present embodiment.

If the user selects "Analysis", the system displays four options: "EDX", "FTIR", "Integration" and "Cancel", as shown in FIG. 4. If "EDX" is selected, the system initiates the analysis of the foreign object based on only the energy dispersive fluorescent X-ray analysis data (EDX data). If "FTIR" is selected, the system initiates the analysis of the foreign object based on only the Fourier transform infrared spectral data (FTIR data). If "Integration" is selected, the system initiates the analysis of the foreign object based on both of the EDX and FTIR data. Selecting "Cancel" makes the system return to the window shown in FIG. 3.

If the user selects "EDX", the system displays a window prompting the user to specify the EDX data file of the foreign object. When the EDX data file is specified by the user, the measurement data comparator 12 reads, from the EDX data in the specified file, the quantitative values of the elements contained in the sample. Subsequently, the comparator 12 compares the read quantitative values with those included in the EDX data of the reference objects stored in the EDX-DB 111, and determines the degree of matching of each reference object with the foreign object. Specifically, for example, the absolute value of the difference between the quantitative value of an element contained in the foreign object and that of the same element contained in the reference object is calculated for each element concerned, and the total of the calculated absolute values ("degree of difference") is subtracted from a predetermined value to obtain the degree of matching. In many cases, the quantitative values of the foreign object and reference objects used in the calculation are semi-quantitative values of the elements concerned, i.e. the quantitative values determined by the FP method in which the measured intensity of the X-ray fluorescence is reproduced using a theoretical formula based on an assumed composition of the principal components of the foreign (or reference) object. Needless to say, quantitative values determined by the calibration curve method may also be used.

Figure 5:
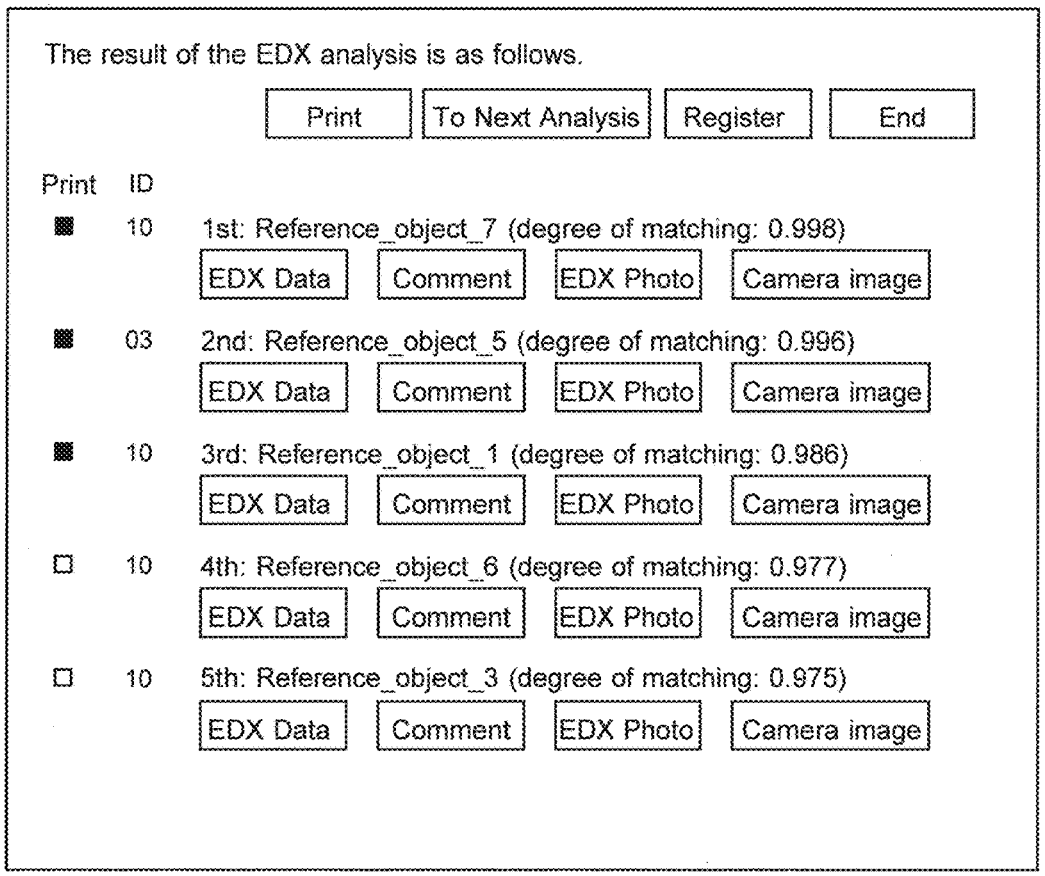
FIG. 5 is one example of the analysis result window displayed by the sample-analyzing system of the present embodiment.

After the degrees of matching of the reference objects with the foreign object are determined by the measurement data comparator 12, the comparison result output section 16 displays a predetermined number of reference objects in descending order of the degree of matching on the display unit 30. FIG. 5 shows one example, in which five reference objects are displayed in descending order of the degree of matching. The user can check this result and identify the foreign object as the reference object having the highest degree of matching. The comparison result output section 16 may also be configured so as to display all reference objects whose degrees of matching are not lower than a specific value, or display only the reference object having the highest degree of matching.

On the window shown in FIG. 5, if the user selects the checkbox displayed along with each reference object, the checkbox turns from white to black (a black checkbox indicates the selected state). Subsequently, if the user presses the print button in the upper area of the window, the measurement data and other items of information for the selected reference objects stored in the EDX-DB 111 are printed out. By pressing any of the buttons labelled "EDX Data", "Comment", "EDX Photo" and "Camera Image" displayed for each reference object, the user can view these kinds of data related to the corresponding reference object on the screen. Pressing the "To Next Analysis" button in the upper area of the screen makes the system return to the window shown in FIG. 4. If the "Register" button is pressed, the EDX data of the currently analyzed foreign object are additionally registered in the EDX-DB 111 as the EDX data of a new reference object.

If the user selects "FTIR", the measurement data comparator 12 similarly prompts the user to specify the FTIR data file of the foreign object. Subsequently, the comparator 12 reads spectrum data from the specified FTIR data file, compares the read data with the spectrum data of a plurality of reference objects stored in the FTIR-DB 112, and determines the degree of matching of each reference object with the foreign object. Specifically, for example, the degree of matching with the foreign object is determined by comparing the peak position (in wavenumber or wavelength) and peak height (or peak area) of each absorption peak included in the spectrum data.

After the degrees of matching of the reference objects with the foreign object are determined by the measurement data comparator 12, the comparison result output section 16 displays a predetermined number of reference objects in descending order of the degree of matching (in a similar window to FIG. 5) on the display unit 30. The displayed information enables the user to identify the foreign object. Once again, the comparison result output section 16 may be configured so as to display all reference objects whose degrees of matching are not lower than a specific value, or to display only the reference object having the highest degree of matching.

The hereinafter described "Integration" process is one of the features of the sample-analyzing system of the present embodiment.

If the user selects "Integration", the measurement data comparator 12 prompts the user to specify both the EDX data file and the FTIR data file. After the EDX data file and the FTIR data file are specified by the user, the comparator 12 reads the quantitative values of the elements contained in the foreign object from the EDX data file as well as the spectrum data from the FTIR data file. Subsequently, for each reference object, the comparator 12 determines the degree of matching of the EDX data and that of the FTIR data.

Additionally, in the case where "Integration" is selected by the user, the scattered radiation intensity ratio calculator 13 reads the measurement conditions and the profile (i.e. the spectrum obtained in the measurement) from the EDX data file. Subsequently, the calculator 13 determines the intensity of the Compton scattered radiation (whose peak is located at an energy position different from the irradiation X-ray) and that of the Rayleigh scattered radiation (whose peak is located at the same energy position as the irradiation X-ray) from the spectrum based on the amount of energy of the irradiation X-ray used in the measurement, and calculates their ratio (intensity of the Compton scattered radiation/intensity of the Rayleigh scattered radiation).

Based on this ratio (intensity of the Compton scattered radiation/intensity of the Rayleigh scattered radiation), the coefficient determiner 14 subsequently determines the weighting coefficients for the EDX data and FTIR data ("EDX coefficient" and "FTIR coefficient"). Specifically, if the ratio is not greater than 1.00, the foreign object is identified as an inorganic substance, and the two values of 0.8 and 0.2 are given to the EDX and FTIR coefficients, respectively. If the ratio is greater than 1.00 and equal to or less than 2.00, the foreign object is identified as a mixture of inorganic and organic substances, and a value of 0.5 is given to both the EDX and FTIR coefficients. If the ratio is greater than 2.00, the foreign object is identified as an organic substance, and the two values of 0.2 and 0.8 are given to the EDX and FTIR coefficients, respectively. The number of combinations of the EDX and FTIR coefficients, which is three in the present embodiment, may be increased to define a greater number of subdivisions. Alternatively, the EDX and FTIR coefficients may be determined using an equation with the aforementioned ratio as a variable.

After the EDX and FTIR coefficients are determined by the coefficient determiner 14, the integrated degree-of-matching calculator 15 performs the following calculation for each reference object: The degree of matching based on the EDX data determined for the reference object is multiplied by the EDX coefficient. The degree of matching based on the FTIR data is also multiplied by the FTIR coefficient. The two calculated values are eventually added to obtain the integrated degree of matching for the reference object concerned.

FIG. 6 shows two lists of reference objects having high degrees of matching for the same foreign object, with the left list showing the reference objects selected based on the EDX data (which corresponds to the result obtained when "EDX" is selected in FIG. 4) and the right list showing the reference objects selected based on the FTIR data (which corresponds to the result obtained when "FTIR" is selected in FIG. 4). In this example, there is a discrepancy between the result based on the EDX data and the result based on the FTIR data.

FIG. 7 shows one example of the reference objects listed in descending order of the integrated degree of matching calculated by integrating the degrees of matching shown in FIG. 6 in the case where the foreign object has been identified as a mixture of inorganic and organic substances, and both the EDX and FTIR coefficients are given a value of 0.5. This example demonstrates that, even when there is a discrepancy between two results of the degrees of matching respectively calculated based on two kinds of data, the sample-analyzing system of the present embodiment can combine those degrees of matching into an integrated degree of matching and present the user a single result based on the two kinds of data.

In the sample-analyzing system of the present embodiment, whether the foreign object is an inorganic substance, organic substance or their mixture is determined based on the ratio of the intensity of the Compton scattered radiation to that of the Rayleigh scattered radiation. If the foreign object is an inorganic substance, a set of coefficients which give a higher weight to the EDX measurement data that are suitable for an analysis of inorganic substances are used in the calculation of the integrated degree of matching. If the foreign object is an organic substance, a set of coefficients which give a higher weight to the FTIR measurement data that are suitable for an analysis of organic substances are used in the calculation. Therefore, the integrated degree of matching is appropriately determined according to the nature of the foreign object.

After the integrated degrees of matching for the reference objects are determined, the comparison result output section 16 displays, on the display unit 30, a window which is similar to the window shown in FIG. 5 yet additionally includes an "FTIR" button for viewing the FTIR data of each reference object. The operation invoked by selecting each button is as already described.

As already described with reference to FIG. 5, the sample-analyzing system of the present embodiment can print out a report which shows the analysis result of the foreign object (a set of data concerning the reference objects having high degrees of matching with the foreign object) obtained in the previously described manner. FIG. 8 illustrates one example of the window for setting the items and layout of the report to be printed. The display items area 61 in the left area of the window shows a list of items that can be displayed on the report. The items that can be displayed on the report include: name of the reference object, degree of matching with the foreign object, order of the degree of matching, comment on the reference object (date and time when the reference object was obtained, date and time of the measurement, and other kinds of information), camera image, EDX image, EDX measurement conditions, result of quantitative analysis by EDX, EDX profile, FTIR measurement conditions, as well as FTIR profile (spectrum). When the user moves one of these items into the layout-editing area 62 in the right area of the window by the drag-and-drop operation, a field for displaying the selected item is shown in the layout area. The user can determine the output layout of the report by appropriately adjusting the position and size of each field displayed in the layout area. If the "EDX profile" or "FTIR profile" is selected in the report, the EDX or FTIR profiles of the foreign and reference objects are shown in different colors in a superposed form, allowing the user to check, on the report, to what extent the measurement data of the foreign object agree with those of the reference objects.

Next, an operation performed when "Library" is selected in FIG. 3 is described.

FIG. 9 is one example of the window displayed when "Library" is selected by the user. The library list 71 shown in this window allows the user to view what kinds of information and measurement data related to the plurality of reference objects are stored in the storage section 11. For each combination of the item and reference object, a checkmark is put if the measurement data or information concerned is stored for the reference object concerned, or a character string of "unregistered" is shown if such data or information is not stored. If there are a plurality of registered camera images, the number of images will be displayed along with the checkmark.

When the user selects an unregistered item in the library list 71, the system displays a window which prompts the user to specify a measurement data file (or the like). When the file is specified by the user, the system registers the file in the database. The user can also select a checked item to view a registered content in the database or edit a comment. Pressing the new registration button 72 invokes transition to a window for additionally registering measurement data (or the like) of a new reference object in the database. The text box and search button 73 in the lower area of the window allow the user to search for a reference object registered in the database.

The sample-analyzing system of the present embodiment can also hold additional information in the storage section 11, such as measurement data other than the EDX and FTIR data used to identify foreign objects (e.g. electron micrographs) or information concerning a report created in the past, and manage the additional information by relating them to the EDX data, FTIR data and other items of information via the reference object ID. This enables the sample-analyzing system of the present embodiment to be used for a unified management of the measurement data and other kinds of information of reference objects obtained for various purposes.

The previous embodiment is a mere example and can be appropriately changed within the spirit of the present invention. As opposed to the previous embodiment in which the databases are provided in the storage section 11 of the data processing unit 10, the databases may be located in a separate device connected to the data processing unit 10. They may also be provided as online databases accessible from the data processing unit 10 through a communication network.

In the previous embodiment, the EDX 40 and FTIR 50 are connected to the sample-analyzing system 1. It is not always necessary to connect these analyzing devices. There are analyzing devices other than the EDX that are suitable for an analysis of inorganic substances, such as an atomic absorption photometer or inductively coupled emission analyzer. Measurement data of the foreign object obtained with one of these devices may be used in place of or in addition to the EDX data. Furthermore, a Raman spectrophotometer may be used as the suitable device for an analysis of organic substances to construct a similar system to that of the previous embodiment.

REFERENCE SIGNS LIST

10 . . . Data Processing Unit
11 . . . Storage Section
111 . . . Energy Dispersive Fluorescent X-Ray Analysis Database
112 . . . Fourier Transform Infrared Spectral Database
113 . . . Reference Object Database
12 . . . Measurement Data Comparator
13 . . . Scattered Radiation Intensity Ratio Calculator
14 . . . Coefficient Determiner
15 . . . Integrated Degree-of-Matching Calculator 16 . . . Comparison Result Output Section
20 . . . Input Unit
30 . . . Display Unit
40 . . . Energy Dispersive Fluorescent X-Ray Analyzer
50 . . . Fourier Transform Infrared Spectrophotometer
61 . . . Display Items Area
62 . . . Layout-Editing Area
71 . . . Library List
72 . . . New Registration Button
73 . . . Search Button

The invention claimed is:

1. A sample-analyzing system for identifying a target sample from measurement data of the target sample obtained using a plurality of analyzing devices including a fluorescent X-ray analyzer as well as at least one device selected from an infrared spectrophotometer and a Raman spectrophotometer, the system comprising:
   a) a storage section in which measurement data obtained for each of a plurality of reference objects using each of the analyzing devices are stored;
   b) a measurement data comparator for comparing, for each of the analyzing devices, the measurement data of the target sample with the measurement data of the plurality of reference objects and for determining a degree of matching of the target sample with each of the plurality of reference objects;
   c) an integrated degree-of-matching calculator for calculating an integrated degree of matching for each of the plurality of reference objects by integrating the degrees of matching determined for the plurality of analyzing devices;
   d) a comparison result output section for outputting information concerning a predetermined number of reference objects in descending order of the integrated degree of matching,
   e) a scattered radiation intensity ratio calculator for calculating an intensity ratio between Compton scattered radiation and Rayleigh scattered radiation from the measurement data of the target sample obtained using the fluorescent X-ray analyzer; and
   f) a coefficient determiner for determining, based on the intensity ratio, a coefficient for weighting degrees of matching related to the fluorescent X-ray analyzer and the infrared spectrophotometer or the Raman spectrophotometer, wherein the integrated degree-of-matching calculator calculates the integrated degree of matching after applying the coefficient to the degrees of matching related to the fluorescent X-ray analyzer and the infrared spectrophotometer or the Raman spectrophotometer.

2. The sample-analyzing system according to claim 1,
   wherein the system is configured to apply a coefficient which gives priority to the degrees of matching related to the fluorescent X-ray analyzer when the intensity ratio is less than 1.0,
   wherein the system is configured to apply a coefficient which gives equal weights to both the degree of matching related to the fluorescent X-ray analyzer and the degrees of matching related to the infrared spectrophotometer or Raman spectrophotometer when the intensity ratio is equal to or greater than 1.0 and less than 2.0, and
   wherein the system is configured to apply a coefficient which gives priority to the degrees of matching related to the infrared spectrophotometer or the Raman spectrophotometer when the intensity ratio is greater than 2.0.

* * * * *